United States Patent [19]

Burke

[11] Patent Number: 5,725,596
[45] Date of Patent: Mar. 10, 1998

[54] CLAMP FOR USE WITH A BONE PROSTHESIS

[76] Inventor: Dennis W. Burke, 245 Highland St., Milton, Mass. 02186

[21] Appl. No.: 705,537

[22] Filed: Aug. 29, 1996

Related U.S. Application Data

[62] Division of Ser. No. 451,129, May 26, 1995, Pat. No. 5,624,443, which is a division of Ser. No. 183,077, Jan. 18, 1994, Pat. No. 5,480,453, which is a continuation of Ser. No. 979,615, Nov. 20, 1992, abandoned.

[51] Int. Cl.⁶ ........................................................ A61F 2/36
[52] U.S. Cl. ........................................................ 623/23
[58] Field of Search ........................... 623/23, 22, 18; 606/99, 89, 86, 87, 105, 57; 269/254 CS, 268; 24/523

[56] References Cited

U.S. PATENT DOCUMENTS

| 202,704 | 4/1878 | Clark et al. . | |
|---|---|---|---|
| 2,682,265 | 6/1954 | Collison . | |
| 2,719,522 | 10/1955 | Hudack . | |
| 2,952,282 | 9/1960 | McHenry . | |
| 3,326,254 | 6/1967 | Diehl . | |
| 4,009,712 | 3/1977 | Burstein et al. . | |
| 4,012,796 | 3/1977 | Weisman et al. . | |
| 4,068,324 | 1/1978 | Townley et al. . | |
| 4,153,953 | 5/1979 | Grobbelaar | 623/23 |
| 4,274,163 | 6/1981 | Malcom et al. | 606/94 |
| 4,357,716 | 11/1982 | Brown . | |
| 4,421,112 | 12/1983 | Mains et al. . | |
| 4,535,487 | 8/1985 | Esper et al. . | |

(List continued on next page.)

FOREIGN PATENT DOCUMENTS

| 98224 | 1/1984 | European Pat. Off. . | |
|---|---|---|---|
| 243109 | 10/1987 | European Pat. Off. . | |
| 393608 | 10/1990 | European Pat. Off. . | |
| 0415837 | 3/1991 | European Pat. Off. . | |
| 2528307 | 12/1983 | France . | |
| 2560764 | 9/1985 | France . | |
| 2635675 | 3/1990 | France . | |
| 0869842 | 3/1953 | Germany | 606/96 |
| 1171022 | 8/1985 | U.S.S.R. . | |
| 1424829 | 9/1988 | U.S.S.R. | 623/23 |
| 1454415 | 1/1989 | U.S.S.R. | 606/99 |
| 1644933 | 4/1991 | U.S.S.R. . | |
| 1694120 | 11/1991 | U.S.S.R. . | |
| 8302555 | 8/1983 | WIPO . | |
| 8603962 | 7/1986 | WIPO . | |

OTHER PUBLICATIONS

Zimmer Modular Calcar Hip System–Surgical Technique developed with Steven F. Schutzer, M.D., Hatford Hospital, Hartford Connecticut, printed in the U.S.A., 1992, Zimmer, Inc.

"Total Knee Arthroplasty Using the First Instruments and the Synatomic Total Knee System", DePuy, Inc., 1985.

"MGII Total Knee System", Zimmer, Inc. 1989.

"Concepts in External Fixation," David Seligson and Malcolm Pope 1992, p. 252.

Zimmer Catalog pp. C62–64 and E28–31, 1987.

Ring et al., "Complete Replacement Arthroplasty of the Hip by the Ring Prosthesis," The Journal of Bone and Joint Surgery, 50B, 4, Nov. 1968, pp. 720–731.

"MGII Total Knee Sustem Surgical Technique, Zimmer", Inc., 1989.

Primary Examiner—David Willse
Attorney, Agent, or Firm—Wolf, Greenfield & Sacks, P.C.

[57] ABSTRACT

A prosthetic device for the human hip having elongated fins or other like protrusions which are provided on the underside of a collar and which extend into previously formed slots or grooves in the bone. Either a plurality of fins, or a single fin having a non-rectilinear shape is provided. Apparatus for formation of the grooves in the bone includes a mill guide which can be mounted onto the proximal end of a rasp embedded in a cavity formed in the bone. A milling bit is used in conjunction with the mill guide to form precisely located and shaped grooves into which the fins can seat. A clamp is provided for securing the prosthetic device to the femur while the cement is hardening.

8 Claims, 6 Drawing Sheets

U.S. PATENT DOCUMENTS

| | | |
|---|---|---|
| 4,549,319 | 10/1985 | Meyer . |
| 4,567,885 | 2/1986 | Androphy . |
| 4,623,353 | 11/1986 | Beuchel et al. . |
| 4,633,862 | 1/1987 | Petersen ................................. 606/88 |
| 4,661,112 | 4/1987 | Muller . |
| 4,678,471 | 7/1987 | Nobel et al. . |
| 4,686,971 | 8/1987 | Harris et al. ............................. 606/99 |
| 4,718,413 | 1/1988 | Johnson . |
| 4,718,909 | 1/1988 | Brown . |
| 4,721,104 | 1/1988 | Kaufman et al. . |
| 4,738,256 | 4/1988 | Freeman et al. . |
| 4,757,810 | 7/1988 | Reese . |
| 4,759,350 | 7/1988 | Dunn et al. . |
| 4,770,660 | 9/1988 | Averill et al. . |
| 4,777,942 | 10/1988 | Frey et al. . |
| 4,783,192 | 11/1988 | Wroblewski et al. . |
| 4,787,383 | 11/1988 | Kenna . |
| 4,791,919 | 12/1988 | Elloy et al. . |
| 4,825,857 | 5/1989 | Kenna . |
| 4,892,093 | 1/1990 | Zarnowki et al. . |
| 4,926,847 | 5/1990 | Luckman . |
| 4,936,863 | 6/1990 | Hofmann . |
| 4,944,762 | 7/1990 | Link et al. . |
| 4,946,379 | 8/1990 | Berchem . |
| 5,035,699 | 7/1991 | Coates . |
| 5,037,425 | 8/1991 | Brown . |
| 5,042,983 | 8/1991 | Rayhack . |
| 5,047,032 | 9/1991 | Jellicoe . |
| 5,047,061 | 9/1991 | Brown . |
| 5,098,436 | 3/1992 | Ferrante et al. . |
| 5,100,409 | 3/1992 | Coates et al. . |
| 5,108,452 | 4/1992 | Fallin . |
| 5,116,380 | 5/1992 | Hewka et al. . |
| 5,129,909 | 7/1992 | Sutherland . |
| 5,133,766 | 7/1992 | Halpern . |
| 5,137,536 | 8/1992 | Koshino . |
| 5,163,964 | 11/1992 | Lazzeri et al. . |
| 5,201,769 | 4/1993 | Schutzer . |
| 5,284,482 | 2/1994 | Mikhail . |
| 5,312,216 | 5/1994 | Hogg ......................................... 623/22 |

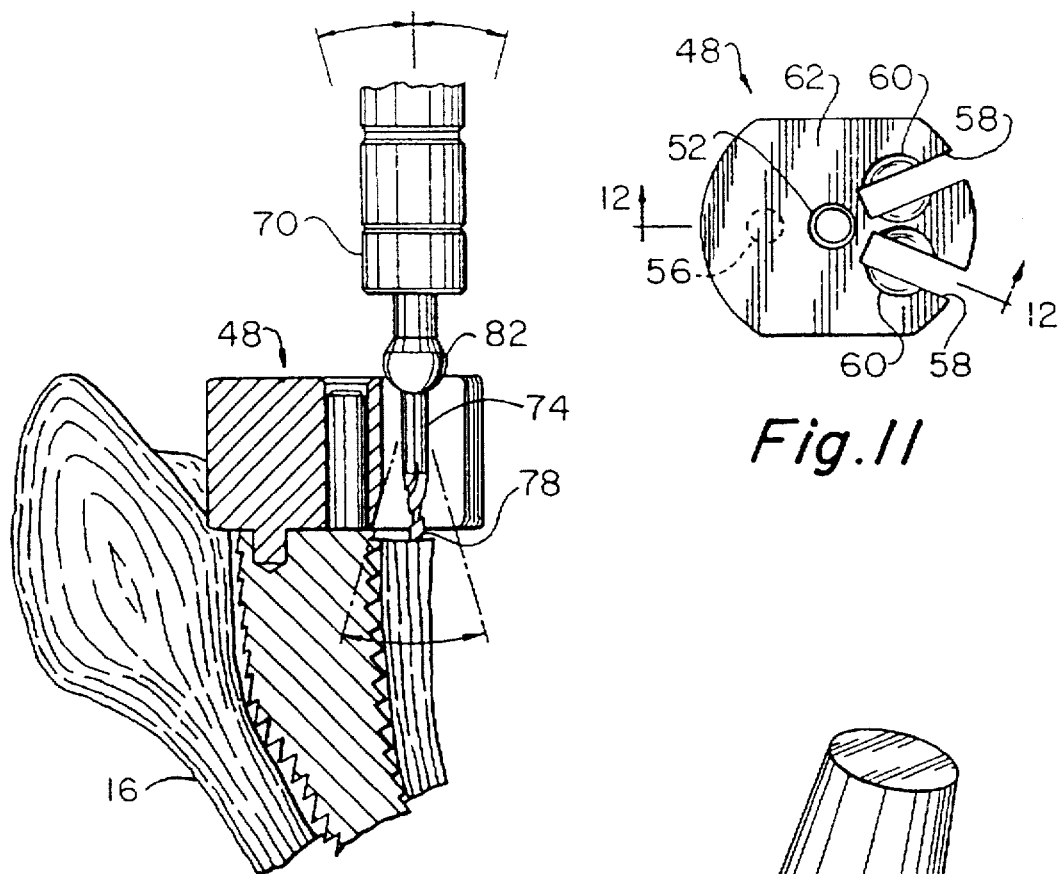
Fig.11
Fig.12
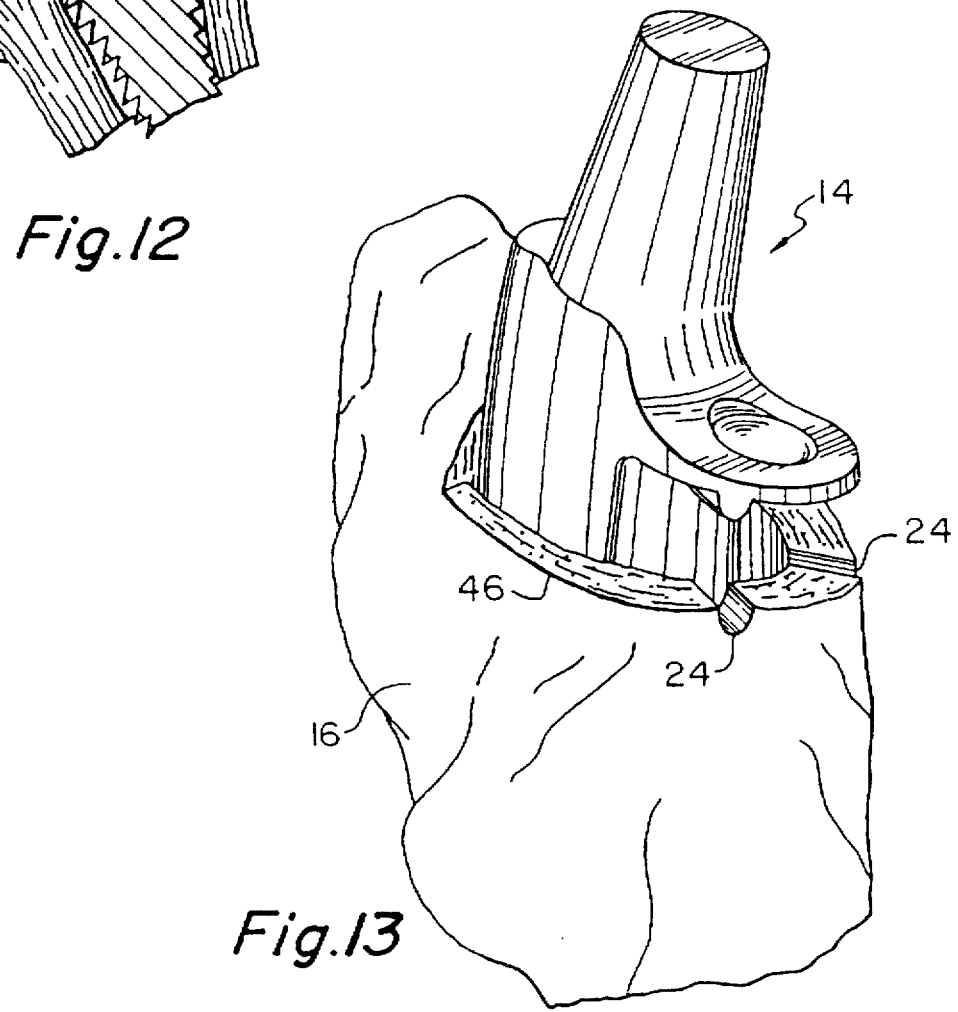
Fig.13

5,725,596

CLAMP FOR USE WITH A BONE PROSTHESIS

This application is a division of application Ser. No. 08/451,129, filed May 26, 1995, entitled CLAMP FOR FEMORAL IMPLANT now U.S. Pat. No. 5,624,443, which is a division of application Ser. No. 08/183,077 filed Jan. 18, 1994, now U.S. Pat. No. 5,480,453, which is a continuation of application Ser. No. 07/979,615, filed Nov. 20, 1992, now abandoned.

FIELD OF THE INVENTION

This invention relates generally to prostheses, and more particularly to femoral components of artificial human hip prostheses.

Background of the Invention

Load-carrying skeletal members, such as the human hip, frequently are rendered non-functional because of fracture, damage, disease, resections for malignancy or disease or because of pain or malformation. Such members are commonly repaired by total joint replacements with artificial components. One type of bone replacement that has been particularly successful over the past thirty years is that of the human hip. Such hip prostheses typically include a femoral portion or component which is implanted in the femur and an acetabular component which is secured to the pelvis. The femoral component includes a head which rotates in a socket formed in the acetabular component. A collar is often provided on the femoral component which rests on a surface on the proximal femur.

Many known hip prostheses require the use of cement for installation of the femoral component into the medullary canal of the femur. One type of cement which is commonly used is methyl methacrylate.

Success of the femoral component of a total hip implant depends in large part on the technical precision with which the implant is inserted. There are several factors which contribute to the success of a femoral component. First, for a cemented component, the component should be centered within the central cavity in the medullary canal of the femur into which the femoral component is inserted. Centering of the component insures that the thickness of the cement mantle surrounding the component is uniform on all sides. Uniformity of the cement mantle renders the load distribution at the bone-cement and metal-cement interfaces generally uniform on all sides of the component, thus avoiding problems associated with overstressing one area of the interface, such as fracturing of the mantle or separation of the mantle from the bone or separation of the component from the mantle.

Another factor which has been identified as contributing to the success of either an uncemented or a cemented femoral component is that the femoral component should be rotated about its axis into the proper angular position with respect to the femur for stability and range of motion. Proper rotational position, or so-called anteversion, allows for accurate reproduction of the mechanical orientation of the hip joint.

A third factor is that the component should be prevented from rotating once it is seated in the femur. For cemented components, such rotational control is very important, particularly during insertion and hardening of the cement, and any false motion while the cement is hardening has been found to be detrimental to the overall results of a cemented femoral stem. Uncontrolled rotation prior to hardening of the cement could result in a stem which is not properly centered and which does not have the proper angular position once the cement hardens. For uncemented components, it is still important that rotational stability be achieved after implantation of the component.

To reduce manufacturing costs and inventory requirements, it is desirable to standardize components to the greatest extent possible, so that one style or design can be used for most patients. Since different sizes of components are required for patients of different stature or age, the manufacture and storage of different styles for each size component is considered highly undesirable. However, the strength, configuration and amount of available bone on the proximal femur varies greater from patient to patient, even for patients who require the same size components. For example, on many patients the bone mass on the proximal femur is so small or is configured such that only a small portion of the collar on the femoral component rests on a bone surface. Thus, standardization requires that the design selected for a component be able to accommodate these large differences in strength, configuration and size.

Many efforts have been made in the past to design components which resist rotation or which tend to be self centering. Examples of such components include those found in the following U.S. Pat. Nos.: 5,116,380; 5,108,452; 4,946,379; 4,936,863; 4,783,192; 4,770,660; 4,678,571; 4,623,353; 4,535,487; 4,068,324; 4,012,796; 2,719,522; and 2,682,265. However, none of the foregoing designs is completely successful in both preventing rotation of the component once implanted, and insuring that the component is held in a properly centered position. In addition, some of the foregoing designs would not operate to prevent rotation or lateral movement in all femurs due to the limited lateral extent of the devices used. In some patients, the devices would not engage any bone because of its irregular configuration or lack of bone mass. Moreover, while spacers, such as those disclosed in U.S. Pat. No. 5,116,380, have been used for the purpose of automatically centering the component within the medullary canal, such spacers do not serve to prevent rotational movement of the prosthesis during cement hardening. Finally, spacers can interfere with the movement of the cement around the edges of the component, thus, on occasion producing voids or gaps in the cement mantle.

It is therefore an object of the present invention to provide an improved femoral component for a hip prosthesis.

It is another object of the present invention to provide a femoral component which is self centering.

It is a further object of the present invention to provide a femoral component which allows the physician to insert and maintain the component with the proper angular position.

It is another further object of the present invention to provide a femoral component which is prevented from rotating or moving laterally during hardening of the cement, and which can be used with many different sizes and shapes of bones.

It is yet another further object of the present invention to provide a method and apparatus for inserting into a femur an improved femoral component.

SUMMARY OF THE INVENTION

These and other objects of this invention are achieved by a femoral component of a prosthetic device for the human hip, in which fins or other like protrusions are provided on the underside of the collar and in which the fins seat in corresponding, previously formed slots or grooves in the proximal femur. These fins or protrusions, and their corresponding mating slots or grooves in the proximal femur position the component so that it is centered within the cavity formed in the medullary canal in the femur and so that the component has the proper angular position or anteversion with respect to the femur. In addition, these fins and their mating grooves prevent rotation and lateral movement of the component during hardening of cement.

In one embodiment, two elongated, non-parallel fins are provided. The two fins can either intersect or they can be spaced apart to form an acute angle with respect to one another. In another embodiment, a single, continuous fin is provided which has a curved or non-rectilinear shape. Regardless of the configuration, the fins can be retrofitted onto existing collars on femoral components, or they may be molded integrally with the collar as it is being formed.

In another aspect of the present invention, a method and apparatus are disclosed for prior formation of the slots or grooves into which the fins extend. A further aspect of the invention relates to a method and apparatus for insertion and cementing of the femoral component into the femur.

The apparatus includes a conventional rasp which is inserted into the medullary canal. The rasp has a post on its proximal end which extends beyond the proximal femur. A mill guide is adapted to be snap-fitted onto the post and is prevented from rotation by a peg extending into the rasp. The mill guide is provided with slots corresponding to the slots or grooves to be formed on the proximal femur. A rounded depression is disposed on the upper surface of the mill guide in association with each Slot. An end mill or milling bit includes an outer housing which has a ball pivot adapted to reside in a corresponding depression on the mill guide. The housing is adapted to be pivoted back and forth about its ball pivot as the milling bit is rotated by a conventional drill motor. The position and depth of penetration of the milling bit is carefully controlled by the mill guide, so that as the milling bit is pivoted, precisely formed slots or grooves are formed on the proximal femur which correspond exactly in size and location to the fins disposed on the undersurface of the collar. The precise positioning of the mill guide allows for proper centering and rotational positioning of the installed femoral component. A clamp is also provided for holding the femoral component in place once it has been inserted into the medullary canal to prevent the component from moving axially out of the canal while the cement is hardening.

In the method of the present invention, a conventional rasp is used to enlarge and clean out the medullary canal of the femur in a conventional manner. Thereafter, the rasp is firmly and securely inserted into the enlarged medullary canal with the desired angular orientation for the femoral component. The proximal femur is then machined in a conventional manner to form a flat and smooth surface. Thereafter, the mill guide is snapped onto the post on the rasp, in the desired rotational orientation. A milling bit with its associated housing is inserted into the mill guide so that the ball pivot of the housing thereof rests in a correspondingly formed depression in the mill guide. The milling bit is positioned to extend a predetermined distance below the base of the mill guide so that it engages the bone surface of the proximal femur. As the drill is activated, the milling bit is pivoted back and forth along a preformed slot in the mill guide for formation of the desired groove or slot in the proximal femur. This process is repeated for each of the slots in the mill guide if more than one fin is desired. Once this process has been completed, the femoral component is inserted so that fins on the lower surface of the collar seat in the correspondingly formed slots or grooves in the proximal femur. Thereafter the component is clamped to the femur.

The apparatus and method of this invention centers the component in the cavity formed in the medullary canal, replicates the proper anteversion, prevents rotation of the component once seated and insures better bond by clamping the component during hardening of the cement. This apparatus and method may be used in conjunction with either cemented or uncemented components.

DESCRIPTION OF THE DRAWINGS

The invention will be more fully appreciated from the following detailed description when taken in conjunction with the accompanying drawings, in which:

FIG. 11 is a top view of the mill guide;

FIG. 12 is a partially cutaway, cross-sectional side view of the proximal femur and mill guide illustrating use of the milling bit to form a slot in the proximal femur;

FIG. 13 is a top perspective view illustrating insertion of the prosthetic hip implant of this invention into the medullary canal of the proximal femur;

DESCRIPTION OF THE PREFERRED EMBODIMENTS

Figure 1:
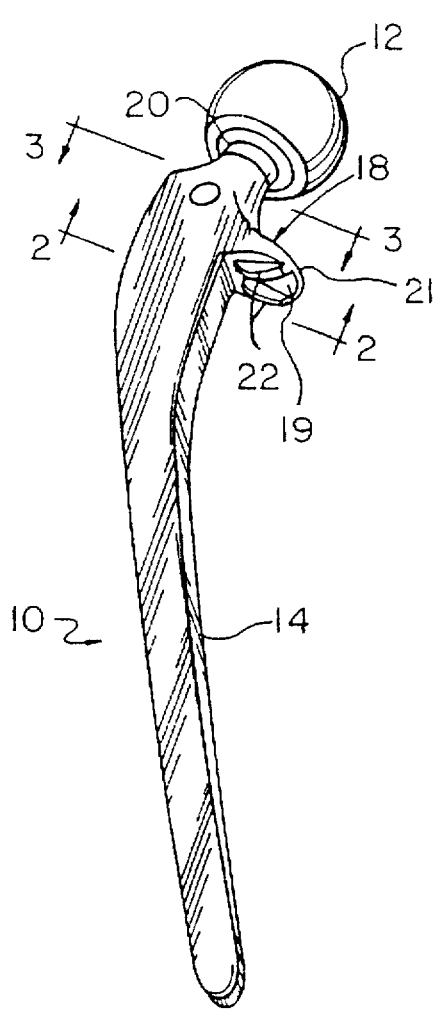
FIG. 1 is a perspective view of a prosthetic hip implant showing the fins of the present invention.
Figure 2:
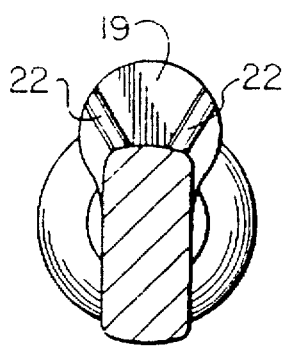
FIG. 2 is a cross-sectional bottom view taken along the line 2—2 of FIG. 1 just below the collar.

With reference now to the drawings, and more particularly to FIG. 1 thereof, one embodiment of this invention will be described in conjunction with a femoral component 10. It is to be understood that component 10 can be implanted either with or without cement. Component 10 includes a femoral head 12 and a femoral stem 14 which is adapted to be inserted into a cavity formed in the medullary canal of a femur 16 (see FIG. 13). Stem 14 includes a large, flat laterally extending collar 18 having a lower surface 19. Surface 19 of collar 18 is adapted to rest on the cortical bone of the proximal femur in the region of the natural femoral neck. Typically, head 12 is coupled to stem 14 by a Morse cone femoral neck 20 connected to collar 18. When head 12 is inserted onto neck 20, a very firm friction fit is formed, and no additional fasteners are required. Head 12 may be readily removed by proper twisting and pulling in the event it needs to be changed or replaced for any reason after implantation.

Typically, stem 14 is held in place in the medullary canal of the femur by the use of cement, such as a methyl methacrylate cement. It is preferred that the mantle formed by the cement surrounding stem 14 within the canal be of approximately the same thickness on all sides of stem 14. Thus, stem 14 should be centered within the canal. In addition, it is highly desirable that accurate replication of the anteversion selected during insertion of the trial implants be achieved. Finally, stem 18 should not be permitted to move while the cement is hardening.

To achieve these results, fins 22 are provided on lower Surface 19 of collar 18. Fins 22 are adapted to seat in correspondingly formed slots or grooves 24 (FIG. 9) on surface 46 (FIG. 5) of the proximal femur. To perform the three functions set forth above, and to provide a configuration that will perform these functions when used with most femurs, regardless of strength, shape, size and available bone surface, it is preferred that there be at least two non-parallel fins 22 formed on lower surface 19 of collar 18, or a single non-rectilinear fin having non-parallel portions. In one embodiment as shown in FIGS. 1–4, two separate, spaced fins 22 are provided. Each fin 22 has a length greater than its width and projects from lower surface 19 of collar 18. Preferably fins 22 extend from the outer edge 21 of collar 18 to a point where they almost touch stem 14. In the embodiments of FIGS. 1–4, fins 22 form an acute angle with respect to one another, but do not touch. Fins 22 converge towards one another in the direction of stem 14, and diverge away from one another in the direction facing away from stem 14.

Other embodiments of this invention are illustrated in FIGS. 5–8. With respect to FIGS. 5 and 6, a single fin 30 is provided on surface 19 of collar 18. Fin 30 has a curved, semi-circular or semi-elliptical configuration in which ends 32 face outwardly away from stem 14 and the closed or curved portion is adjacent item 14. Fin 30 can have any shape or radius of curvature, so long as it is non-rectilinear and so long as it extends a substantial distance across surface 21 of collar 18.

Figure 7:
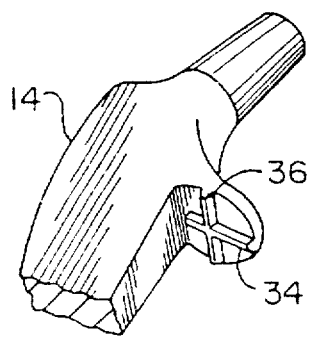
FIG. 7 is a cutaway, perspective bottom view of a prosthetic hip implant showing yet another embodiment of the fins of this invention.
Figure 8:
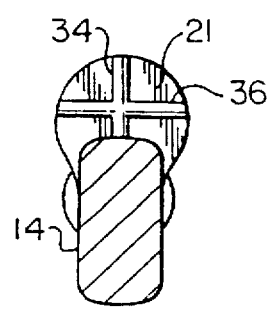
FIG. 8 is a bottom elevational view of the implant of FIG. 7.

In FIGS. 7 and 8, two fins 34 and 36 are provided. Fins 34 and 36 are generally orthogonal to one another, and intersect one another at a single point. Preferably, fin 34 extends from edge 21 almost to the surface of stem 14, while fin 36 traverses almost the entire distance laterally across the surface 19 of collar 18. Fins 34 and 36 typically form a plus sign or cross configuration. However, fins 34 and 36 could be disposed at an angle other than 90° with respect to one another, so long as they are not parallel to one another.

Fins 22, 30, 34 and 36 can be either milled from the material of collar 18 and formed integrally therewith, or they can be bonded or retrofitted to surface 19 of collar 18 after collar 18 has been formed. In the latter embodiment, fins 22, 30, 34 and 36 could be formed of methyl methacrylate cement which has been molded into the desired shape and bonded to surface 19 of collar 18.

It will be appreciated that more than two fins could be provided, or other configurations are possible, so long as the fins prevent both rotational movement of the implanted stem 14 with respect to the femur and lateral movement of stem 14 in a direction generally normal to the direction of elongation of the femur. Moreover, the fins must have a configuration which allows corresponding depressions to be readily etched into surface 46 of the proximal femur. Also, the fins must extend sufficiently far across surface 19 of collar 18 that each fin, or each non-parallel portion of the same fin, engages the bone in the proximal femur over a sufficient distance to adequately prevent rotation and lateral movement of stem 14. Preferably, the coverage of the fins on surface 19 of collar 18 should be sufficiently great that all of these requirements are met for patients regardless of the bone strength, configuration, mass or size so that a standard design can be used with most patients.

The method of this invention and the apparatus used to implement this method will now be described with particular reference to FIGS. 9–14. It is to be understood that this same method and apparatus can be used for a cemented or uncemented implant. The tools employed include a rasp or broach 40, mill guide 48, end mill or milling bit 70 and clamp 92. Broach 40 is substantially similar to a conventional broach used for enlarging the medullary canal of a femur. As previously indicated, broach 40 has the same shape as stem 14, but is larger in size. The outer surface of broach 40 is coaxial with the outer surface of stem 14, but the distance between the central axis of broach 40 and its outer surface is greater than the distance between the central axis of stem 14 and its outer surface. Serrations 41 are provided along the outer surface of broach 40 for assisting in the enlarging and cleaning out of the medullary canal to from a cavity. Extending from an upper surface 44 of broach 40 is a shaft 42. Disposed near the upper end of shaft 42 is a recess 50 into which a spring mounted ball (not shown) on an attachment can seat for a snap-fit. A generally circular hole 54 is formed on surface 44 adjacent shaft 42.

Mill guide 48 is used for forming grooves or slots 24 on surface 46. Mill guide 48 includes machined slots 58 which extend from an upper surface 62 to a lower surface 64 of mill guide 48. Mill guide 48 has the same number of slots 58 as there are fins on collar 18. In addition, slots 58 have the same general configuration as the fins on collar 18. Disposed on upper surface 62 in association with each slot 58 is a semi-circular depression 60. Shaft 42 is intended to be inserted into a channel 52 of mill guide 48, and a spring mounted ball (not shown) in channel 52 provides a snug snap-fit of mill guide onto shaft 42.

Milling bit 70 is utilized to machine grooves Milling bit 70 has a rotatable shaft 74 and outer housing 72 which does not rotate and is coaxial with shaft 74. Proximal end 76 of shaft 74 is adapted to be mounted into a chuck of a conventional drill, while distal end 78 is provided with a milling tip which is adapted to cut bone. A shoulder 80 provided adjacent proximal end 76 limits axial movement of shaft 74 with respect to housing 72. Generally spherical ball 82 is disposed at the lower end of housing 72 and is adapted to seat in depression 60 of mill guide 48.

The uses of these tools to perform the method of the present invention will now be described. Initially, the femur is prepared for surgery in a conventional manner. Rasp or broach 40 is used to clean out and enlarge the medullary canal to form a cavity in the center of the femur to prepare for insertion of stem 14, so that the outer surfaces of stem 14 are spaced a predetermined distance from the inner surface of the cavity formed.

In a conventional manner, the upper surface of the proximal femur is milled smooth and flush with the upper surface 44 of broach 40 to provide a relatively flat surface 46 on the proximal femur upon which surface 19 of collar 18 can rest. This process is typically accomplished using a large rotatable milling tool (not shown) which is mounted on shaft 42 and is rotated by a conventional drill (not shown). Once surface 46 has been prepared as described, mill guide 48 is snapped onto shaft 42. Recess 50 cooperates with a spring mounted ball (not shown) within channel 52 to hold mill guide 48 snugly in place so that lower surface 64 is in contact with surface 44. Peg 56 disposed on lower surface 64 resides in cooperatively formed hole 54 in surface 44 to prevent mill guide 48 from rotating with respect to shaft 42.

A slot 58 is provided for each fin 22. Slots 58 of mill guide 48 are configured to provide a slot or groove 24 on surface 46 of the proximal femur which corresponds almost precisely to the size and shape of the selected fins 22 or 30 or 34 and 36 to be provided on collar 18. If, for example, fins 22 have the shape and configuration as shown in FIG. 1, slots 58 would have the shape and configuration shown in FIG. 11. If, on the other hand, a fin 30 is to be utilized, a single slot would be provided in mill guide 48 having the same semi-circular shape or semi-elliptical configuration of fin 30. In this event, only a single depression 60 would be provided on surface 62 at roughly the center of the slot. If fins 34 and 36 are to be utilized, two intersecting slots would be provided in mill guide 48, and a single depression 60 would be disposed on surface 62 at the point of intersection of the slots.

Figures 9, 10:
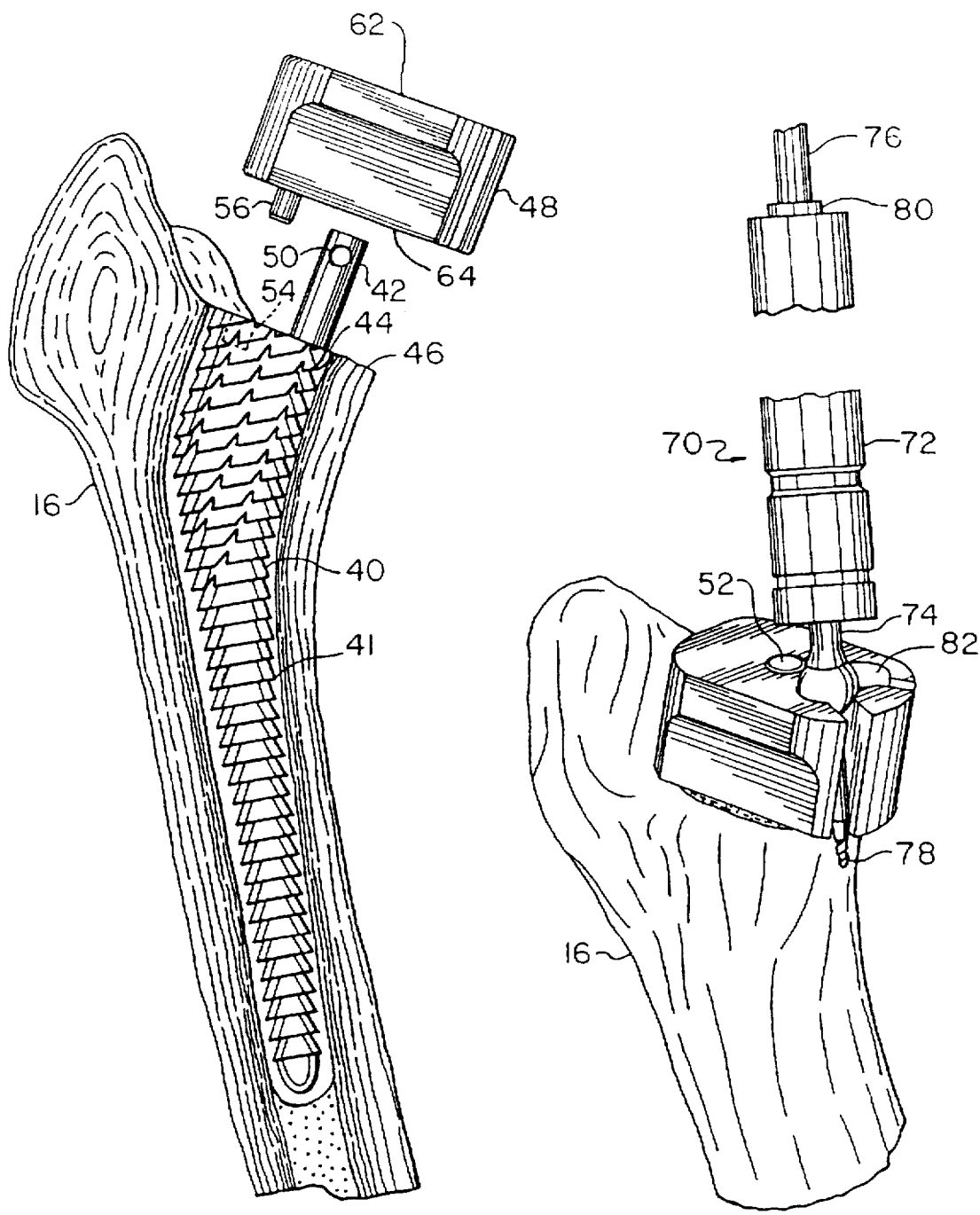
FIG. 9 is a cross-sectional side view of a femur showing the rasp and the snap-on mill guide.
FIG. 10 is a perspective view showing use of the mill guide and milling bit to form a slot in the proximal femur.

The manner of creation of these slots or grooves 24 will now be described with reference to FIGS. 10 and 12. Milling bit 70 is utilized for this purpose. Shoulder 80 is pushed into abutment with proximal end 84 of housing 72, and ball 82 is seated in cooperatively formed depression 60. Thereafter, the drill is activated and distal end 78 of shaft 74 penetrates surface 46 of the proximal end of femur 16 to substantially the same depth as fin 22 when surface 19 of collar 18 rests on surface 46. Groove 24 is formed by pivoting housing 72 about ball 82 to move shaft 74 back and forth through slot 58 while shaft 74 is being rotated by a drill (not shown). In this way, the cutting of each groove 24 is precisely controlled and each groove 24 is formed with the desired location, depth and width.

Using this method, groove 24 will be deepest at a point directly below depression 60 and shallowest at points spaced farthest from depression 60 in a direction parallel to surface 46. This groove 24 will have a somewhat arcuate shape with a radius equal to the distance from the center of ball 82 to the tip of distal end 78. Accordingly, fins 22, 30, 34 and 36 preferably have the same arcuate shape with the same radius of curvature. Also, fins 22, 30, 34 and 36, if viewed from the end, preferably have a U-shaped configuration to conform to the U-shaped cross-sectional configuration of recess 24 as formed by tip 78.

Once the foregoing process has been completed, and grooves 24 have been formed, milling bit 70, mill guide 48 and broach 40 are all removed from the femur and stem 14 is inserted as shown in FIG. 13. Fins 22 are inserted into corresponding grooves 24, and preferably force is applied to the upper surface of component 10 to drive it downwardly into the femur so that fins 22 seat securely and tightly in grooves The insertion of stem 14 is accomplished in conjunction with the provision of cement within the cavity in the medullary canal within femur 16, in a conventional manner. Fins 22 automatically center stem 14 within the medullary canal to produce a uniform mantle, to prevent rotation of component 10 during the time the cement is curing, and to produce precise replication of anteversion.

Figure 3:
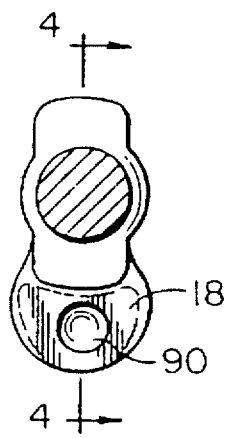
FIG. 3 is a cross-sectional top view taken along the line 3—3 of FIG. 1 just above the collar.
Figure 4:
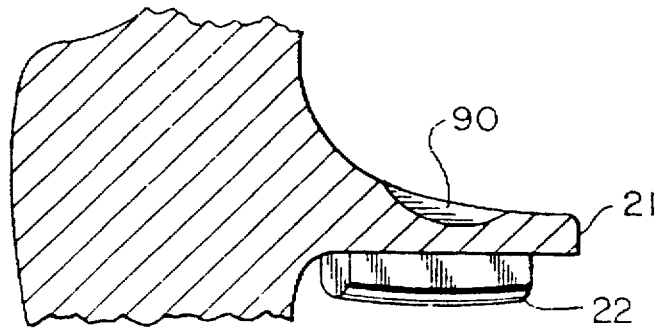
FIG. 4 is a cross-sectional side view taken along the line 4—4 of FIG. 3.
Figure 15:
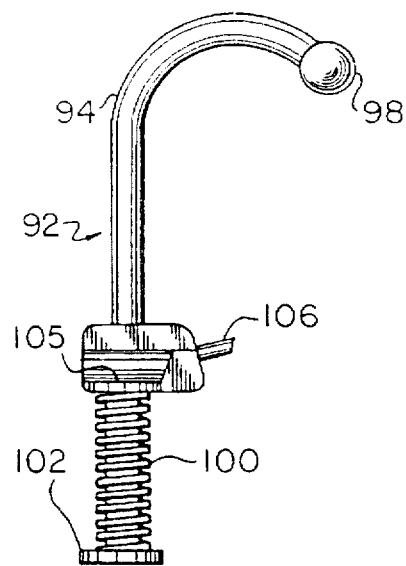
FIG. 15 is a side elevational view of the clamp shown in FIG. 14.
Figure 16:
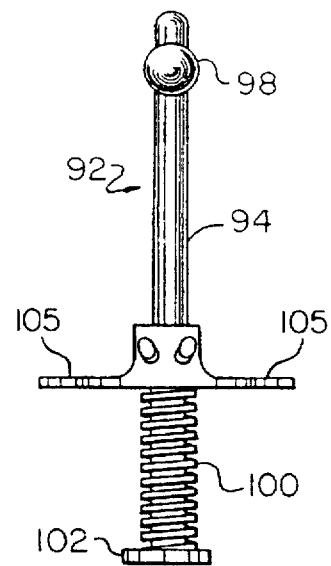
FIG. 16 is a front elevational view of the clamp of FIG. 15.
Figure 5:
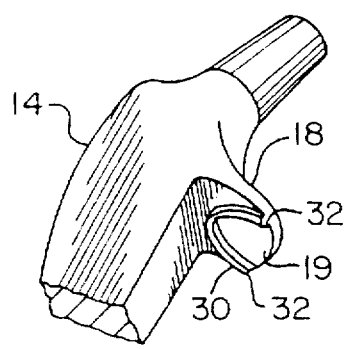
FIG. 5 is a cutaway, perspective bottom view of a prosthetic hip implant showing another embodiment of the fins of this invention.
Figure 6:
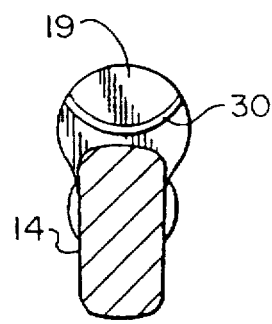
FIG. 6 is a bottom elevational view of the implant of FIG. 5.

Another feature of this invention will now be described with particular reference to FIGS. 3, 4 and 14–16. As is shown in FIGS. 3 and 4, a depression 90 is formed in the upper surface of collar 18. A clamp 92 is used in conjunction with depression 90 to provide a downward force on stem 14 while the cement is hardening to make certain that surface 19 of collar 18 is urged snugly against surface 46, and that fins 22 are seated in corresponding grooves 24 so that the resulting bond is tight and so that component 10 is in precisely the desired rotational and lateral orientation.

Clamp 92 includes a stem 94 having an arcuate upper portion 96, a ball 98 secured to the distal end of upper portion 96, a carriage 104, a flange 102 and a compression spring 100. Stem 94 extends through a hole in carriage 104, and carriage 104 slides along stem 94. A set screw (not shown) in carriage 104 rides in an axially extending slot along stem 94 (not shown) to limit axial travel of carriage 104, and to prevent rotational movement of carriage 104 with respect to stem 94. Carriage 104 includes one or more spikes 106, which extend from one side thereof toward ball 98, and finger grips 105. Spring 100 is captured between carriage 104 and flange 102 and urges carriage 104 in a direction away from flange 102.

Figure 14:
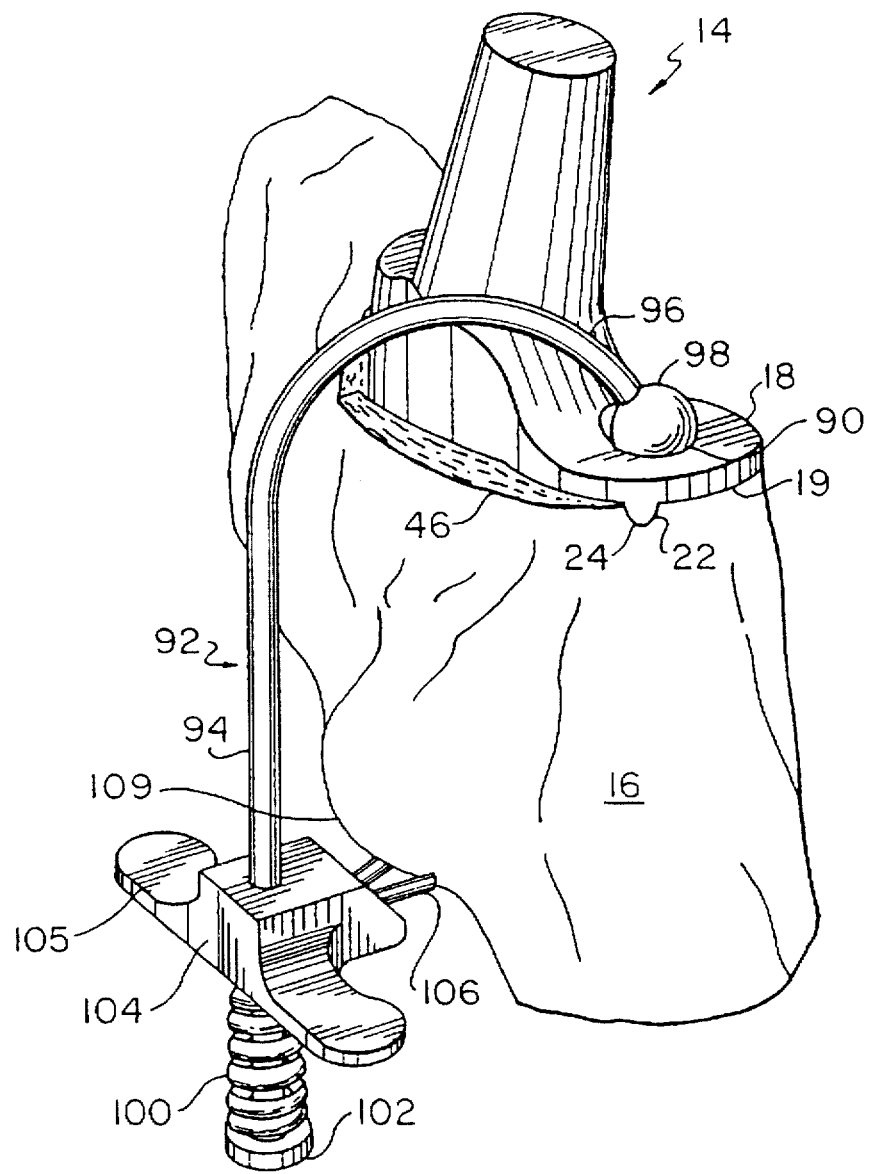
FIG. 14 is a perspective view showing the prosthetic hip implant of this invention being clamped into position on the proximal femur during hardening of the cement.

Use of clamp 92 will now be described with particular reference to FIG. 14. Ball 98 is seated or nested in depression 90 in collar 18. With a thumb pressing against flange 102, and two fingers pressing downwardly on finger grips 105, carriage 104 is withdrawn downwardly towards flange 102. At the same time spikes 106 are driven into engagement with the lesser trochantor. As the downward pressure on carriage 104 is released, spikes 106 dig into the lesser trochantor, and spring 100 biases stem 94 so that ball 98 is urged toward carriage 104. Spring 100 thereby applies a downward pressure to ball 98 which then urges component 10 downwardly to properly seat stem 14 within femur 16. Clamp 92 is removed once the cement has properly hardened. Removal is accomplished by compressing spring 100 between carriage 104 and flange 102 and withdrawing spikes 106 from the lessor trochantor.

Clamp 92 applies the requisite seating force to component 10 with little damage to the bone or surrounding tissues. Clamp 92 is easily operated and readily removed by the physician.

Figure 18:
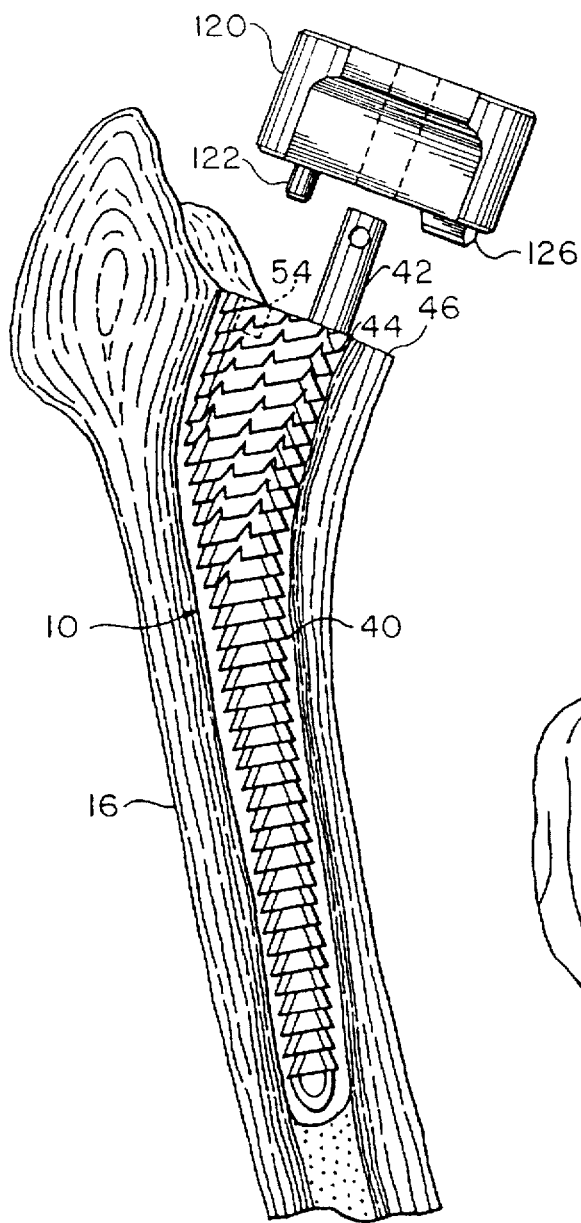
FIG. 18 is a partially cutaway, cross-sectional side view of the proximal femur illustrating use of the stamp of FIG. 17.
Figure 17:
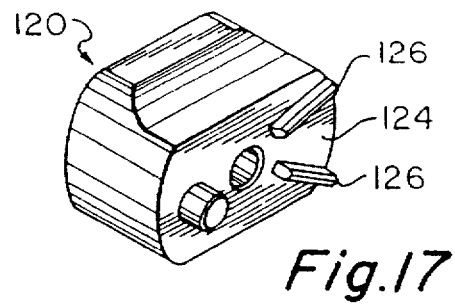
FIG. 17 is a perspective view of a stamp employed in another embodiment of the method for forming the slots in the proximal femur.
Figure 19:
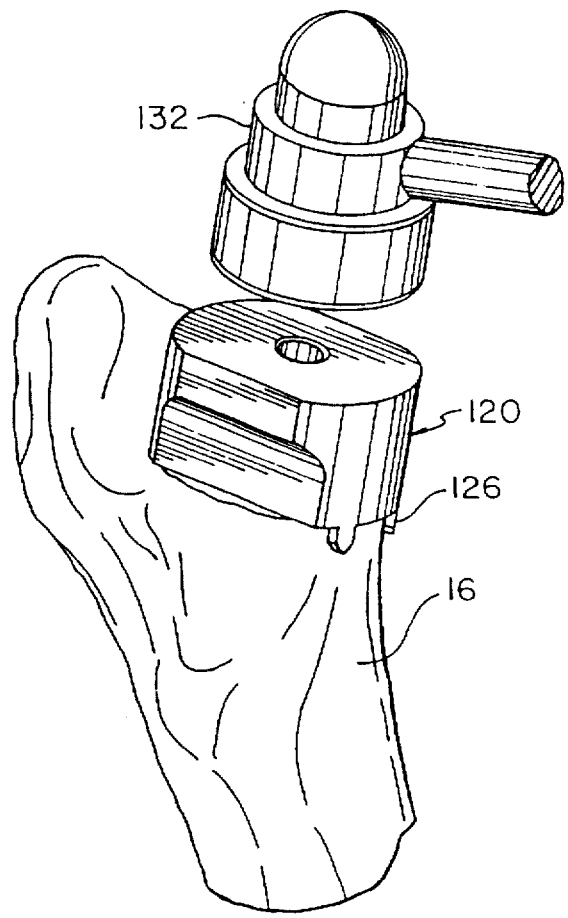
FIG. 19 is a perspective view further illustrating the use of the stamp of FIG. 17.

Another embodiment of this invention will now be described with reference to FIGS. 17–19. This embodiment can be used either with or without cement. Like numbers are used for like parts, where applicable. In this embodiment, fins again are disposed on surface 19 of collar 18 of component 10. These fins may have any one of the shapes previously described, particularly with respect to FIGS. 2–8. In this embodiment, as in the previous embodiments, corresponding grooves are cut into surface 46 of the proximal femur for accepting the fins, prior to implantation of the component. This embodiment differs from that of FIGS. 9–12 in the manner of formation of the grooves for accepting the fins.

In this embodiment, instead of mill guide 48, a stamp 120 is mounted onto shaft 42 of broach 40. Stamp 120 includes a peg 122 which extends into hole 54 for proper orientation of stamp 120 and for preventing rotation of stamp 120 during the cutting process. Projections 126 on lower surface 124 of stamp 120 have sharpened edges along the surface thereof confronting surface 46 of the proximal femur. Projections 126 have precisely the same shape, orientation and size as fins 22, 30 or 34 and 36 disposed on surface 19 of collar 18. Once stamp 120 has been mounted onto shaft 42, stamp 120 is driven downwardly against surface 46 by a hammer 132, or other like tool for applying force, to drive projections 126 into surface 46 of the proximal femur. This operation stamps into surface 46 grooves which have exactly the same size, shape and orientation as selected fins 22, 30 or 34 and 36. Once surface 124 has been driven into firm and uniform contact with surface 44, stamp 120 and broach 40 are removed. Component 10 is thereafter inserted as previously described, so that the fins seat in the grooves formed in surface 46 of the proximal femur. Thereafter, the implantation process is completed, precisely as described previously with respect to the embodiments of FIGS. 9–12.

Typically, shaft 42, mill guide 48, shaft 74 of milling bit 70, clamp 92 and plate 120 are all formed of a hard, corrosion resistant material such as stainless steel. However, other known, hard materials may be used. For purposes of illustration only, typical dimensions of the fins of this invention will be provided. However, it is to be understood, that by providing such examples, the scope of the invention is in no way limited. In a typical implant, fins 22 would each have a length of about 1 cm and a width of about 1 mm. Fin 30 would have an approximate radius of curvature of 1 cm and a total length between ends 32 of about 15 mm. Fins 34 and 36 would typically each have a length of about 1 cm. The sizes and shapes of the tools used for implantation, as described herein, would be selected in accordance with the sizes and shapes of the particular femur upon which the surgical operation is being performed.

The foregoing invention provides a method and apparatus for centering a stem within the cavity in the medullary canal of the femur, permitting accurate reproduction of anteversion, preventing rotation once the prosthetic has been seated, and clamping the prosthetic during seating to insure a good cement bond. As a result, a uniform mantle of cement is provided around the circumference of the stem which optimizes load distribution between the bone-cement and metal-cement interfaces, thus rendering less likely failure due to nonevenly distributed stresses. Accurate reproduction of anteversion improves the quality of the implant and improves relative movement within the joint so that the patient can enjoy more nearly normal and pain-free activity. Rotational control prevents false movement while the cement is hardening insuring proper rotational orientation and improving the chances of a better cement bond and longer life for the prosthetic. Clamping during seating also insures a better and tightly cemented bond. The method and apparatus of this invention also have applicability to uncemented components since they permit accurate reproduction of anteversion and prevent rotational movement of the prosthetic once it has been implanted.

In view of the above description, it is likely that modifications and improvements will occur to those skilled in the art which are within the scope of this invention. The above description is intended to be exemplary only, the scope of the invention being defined by the following claims and their equivalents.

What is claimed is:

1. A combination comprising:
   a femoral hip prosthesis including an elongated stem adapted to fit into a cavity formed on an upper proximal surface of a bone and a collar extending from a proximal end of said stem in a direction generally transverse to a direction of elongation of the stem, said collar having an upper surface and a lower surface, the lower surface of said collar being adapted to rest in contact with the upper proximal surface of the bone; and
   apparatus structured to clamp said femoral hip prosthesis into the cavity of the bone, said apparatus comprising:
   a first portion engaging the upper surface of said collar at a location spaced in the direction generally transverse to the direction of elongation of said stem from said stem of said femoral hip prosthesis;
   a second portion structured to engage the bone, said second portion being interconnected with said first portion; and
   apparatus interconnecting said first portion and said second portion and applying a force between said first portion and said second portion for providing clamping of said femoral hip prosthesis in the bone.

2. The combination of claim 1 wherein said second portion includes a spike for engaging the bone and wherein said first portion includes a curved surface for seating in a correspondingly formed recess disposed on the upper surface of the collar of the femoral hip prosthesis.

3. A combination comprising:
   a femoral hip prosthesis including an elongated stem adapted to fit into a cavity formed on an upper proximal surface of a bone and an exposed upper surface having a curved recess formed thereon, said curved recess being spaced from said stem in a direction generally transverse to a direction of elongation of said stem; and
   apparatus structured to clamp said femoral hip prosthesis into the cavity of the bone, said apparatus comprising:
   a first portion engaging the exposed upper surface of said femoral hip prosthesis, said first portion including a curved surface corresponding to said curved recess and seating therein;
   a second portion structured to engage the bone, said second portion being interconnected with said first portion; and
   apparatus interconnecting said first portion and said second portion and applying a force between said first portion and said second portion for providing clamping of said femoral hip prosthesis in the bone.

4. The combination of claim 3 wherein said second portion includes a spike for engaging the bone and wherein said first portion includes a ball for seating in said correspondingly formed recess disposed on the exposed upper surface of the femoral hip prosthesis.

5. A combination comprising:
   a prosthesis including an elongated stem adapted to fit into a cavity formed on an upper proximal surface of a bone and a collar extending from a proximal end of said stem in a direction generally transverse to a direction of elongation of said stem, said collar having an upper surface and a lower surface, the lower surface of said collar being adapted to rest in contact with the upper proximal surface of the bone; and
   apparatus structured to clamp said prosthesis into the cavity of the bone, said apparatus comprising:
   a first portion engaging the upper surface of said collar at a location spaced in the direction generally transverse to the direction of elongation of said stem from said stem of said prosthesis;
   a second portion structured to engage the bone, said second portion being interconnected with said first portion; and apparatus interconnecting said first portion and said second portion and applying a force between said first portion and said second portion for providing clamping of said prosthesis in the bone.

6. A combination comprising:

a prosthesis including an elongated stem adapted to fit into a cavity formed on an upper proximal surface of a bone and an exposed upper surface having a curved recess formed thereon, said curved recess being spaced from said stem in a direction generally transverse to a direction of elongation of said stem; and apparatus structured to clamp said prosthesis into the cavity of the bone, said apparatus comprising:

a first portion engaging the exposed upper surface of said prosthesis, said first portion including a curved surface corresponding to said curved recess and seating therein;

a second portion structured to engage the bone, said second portion being interconnected with said first portion; and apparatus interconnecting said first portion and said second portion and applying a force between said first portion and said second portion for providing clamping of said prosthesis in the bone.

7. A combination comprising:

a femoral hip prosthesis including an elongated stem adapted to fit into a cavity formed on an upper proximal surface of a bone and a collar extending from a proximal end of said stem in a direction generally transverse to a direction of elongation of said stem, said collar having an upper surface and a lower surface, the lower surface of said collar being adapted to rest in contact with the upper proximal surface of the bone, said upper surface of said collar including a curved recess; and apparatus structured to clamp said femoral hip prosthesis into the cavity of the bone, said apparatus comprising:

a first portion engaging the upper surface of said collar at a location spaced from said stem in the direction generally transverse to the direction of elongation of said stem, said first portion including a ball seating in said recess disposed on the upper surface of said collar of said femoral hip prosthesis;

a second portion including a spike structured to engage the bone, said second portion being interconnected with said first portion; and apparatus interconnecting said first portion and said second portion and applying a force between said first portion and said second portion for providing clamping of said femoral hip prosthesis in the bone.

8. A combination comprising:

a femoral hip prosthesis including an elongated stem adapted to fit into a cavity formed on an upper proximal surface of a bone and an exposed upper surface having a curved recess formed thereon, said curved recess being spaced from said stem in a direction generally transverse to a direction of elongation of said stem; and apparatus structured to clamp said femoral hip prosthesis into the cavity of the bone, said apparatus comprising:

a first portion engaging the exposed upper surface of said femoral hip prosthesis, said first portion including a ball corresponding to said curved recess and seating therein;

a second portion including a spike structured to engage the bone, said second portion being interconnected with said first portion; and apparatus interconnecting said first portion and said second portion and applying a force between said first portion and said second portion for providing clamping of said femoral hip prosthesis in the bone.

* * * * *